United States Patent
Donnet et al.

(10) Patent No.: US 9,987,459 B2
(45) Date of Patent: Jun. 5, 2018

(54) DEVICE FOR INDUCING AND MAINTAINING SLEEP

(75) Inventors: Frederick Donnet, Hong Kong (CN); Colin Aston-James, Suffolk (GB)

(73) Assignee: CAMBRIDGE LEARNING TECHNOLOGY LIMITED, Hong Kong (CN)

( * ) Notice: Subject to any disclaimer, the term of this patent is extended or adjusted under 35 U.S.C. 154(b) by 189 days.

(21) Appl. No.: 14/128,462

(22) PCT Filed: Jun. 22, 2012

(86) PCT No.: PCT/EP2012/062139
§ 371 (c)(1),
(2), (4) Date: Mar. 19, 2014

(87) PCT Pub. No.: WO2012/175704
PCT Pub. Date: Dec. 27, 2012

(65) Prior Publication Data
US 2015/0038776 A1    Feb. 5, 2015

(30) Foreign Application Priority Data

Jun. 22, 2011    (EP) .................................. 11171111.5

(51) Int. Cl.
*A61M 21/02*    (2006.01)
*A61M 21/00*    (2006.01)
(Continued)

(52) U.S. Cl.
CPC ............ *A61M 21/02* (2013.01); *A61M 21/00* (2013.01); *G09B 5/04* (2013.01); *G09B 19/00* (2013.01);
(Continued)

(58) Field of Classification Search
CPC .............................. A61M 21/00–21/22; A61M 2021/0005–2021/0088
See application file for complete search history.

(56) References Cited

U.S. PATENT DOCUMENTS 5,135,468 A * 8/1992 Meissner .............. A61M 21/00
                                                                600/28
5,213,562 A    5/1993 Monroe
(Continued)

FOREIGN PATENT DOCUMENTS

CN    101715356    5/2010
WO    9517854    7/1995
(Continued)

OTHER PUBLICATIONS

"Binaural Harmonics." Mind Sync-Home. N.p., Jan. 6, 2010. Web. Dec. 3, 2015.*
(Continued)

*Primary Examiner* — Catherine B Kuhlman
(74) *Attorney, Agent, or Firm* — Koppel, Patrick, Heybl & Philpott (57) ABSTRACT

Described herein is a device (100) for inducing and maintaining sleep in which one of a number of sleep programs can be selected in accordance with the requirement of a user, in addition, a background can be selected by the user which forms part of the program. The device (100) includes a display (120) and a control panel (130) mounted in a housing (110). Individual sleep programs are selected using the control panel (130) and the display (120). The device (100) includes processing unit (140) connected to a memory (150) and a driver (160) for a pair of speakers (170, 175) through which the selected sleep program is played to the user.

33 Claims, 8 Drawing Sheets (51) Int. Cl.
*G09B 5/04* (2006.01)
*G09B 19/00* (2006.01)

(52) U.S. Cl.
CPC ............... *A61M 2021/0027* (2013.01); *A61M 2021/0033* (2013.01); *A61M 2021/0083* (2013.01); *A61M 2205/502* (2013.01); *A61M 2205/52* (2013.01)

(56) References Cited

U.S. PATENT DOCUMENTS

| | | | | |
|---|---|---|---|---|
| 5,356,368 | A * | 10/1994 | Monroe | A61M 21/00 600/28 |
| 7,749,155 | B1 * | 7/2010 | Anderson | A61M 21/00 600/26 |
| 2002/0146469 | A1 * | 10/2002 | Wiegand | A61K 31/00 424/725 |
| 2006/0249004 | A1 | 11/2006 | Bunker et al. | |
| 2008/0304691 | A1 | 12/2008 | Lai | |
| 2010/0076253 | A1 * | 3/2010 | Altman | A61M 21/00 600/28 |
| 2010/0222640 | A1 | 9/2010 | Anderson | |

FOREIGN PATENT DOCUMENTS

| WO | WO95/17854 A1 | 7/1995 | | |
|---|---|---|---|---|
| WO | WO2004/093613 | 11/2004 | | |
| WO | WO 2004093613 A1 * | 11/2004 | ........... | A47G 9/1045 |

OTHER PUBLICATIONS

European Patent Office International Search Report and Written Opinion dated Sep. 19, 2012, International Application No. PCT/EP2012/062139 (3 pages).
European Patent Office International Preliminary Report on Patentability dated Oct. 21, 2013, International Application No. PCT/EP2012/062139 (29 pages).
Response to Second Written Opinion dated Aug. 28, 2013, International Application No. PCT/EP2012/062139 (40 pages).
Demand for International Preliminary Examination dated Feb. 8, 2013, International Application No. PCT/EP2012/062139 (16 pages).
Chinese Office Action, Application No. 201280030641.0, dated Apr. 14, 2015.
European Office Action, Application No. 12730491.3, dated Mar. 13, 2017.
United Kingdom Office Action, Application No. GB1321910.0, dated May 9, 2017.
Japanese Office Action, Application No. 2014-516375, dated Mar. 8, 2016.
Japanese Office Action, Application No. 2014-516375, dated Dec. 2, 2016.
Anonymous: "Review: Pzizz Relax :: App Advice," Oct. 28, 2010, https://web.archive.org/web/20101028033458/http://appadvice.com/appnn/2010/03/review-pzizz-relax/, retrieved Mar. 6, 2017.

* cited by examiner

DEVICE FOR INDUCING AND MAINTAINING SLEEP

FIELD OF THE INVENTION

The present invention relates to a device for inducing and maintaining sleep, and is more particularly concerned with such a device that can be programmed according to the specific needs of the individual.

BACKGROUND TO THE INVENTION

Various methods are known for inducing sleep and include frequency following response (FFR) techniques and the use of binaural tones. In addition, methods are known in which a person can train himself/herself to replicate a desired state of consciousness without the need for audio stimulation. U.S. Pat. No. 5,213,562 discloses such a method and the ability to transfer such states from one individual to another by inducement of a binaural beat phenomenon. This is achieved by using electroencephalography (EEG) signals from one individual superimposed on stereo signals that are applied to another individual.

U.S. Pat. No. 5,356,368 discloses a method that uses FFR to facilitate attainment of desired states of consciousness. Sleep patterns are reproduced based on observed brain patterns during portions of a sleep cycle.

U.S. Pat. No. 4,573,449 discloses a method and apparatus in which sound pulses are emitted by an electro-acoustic transducer to assist a person suffering from sleeplessness to become relaxed and fall asleep. An individual using the device is required to breathe in and out over a predetermined period of time in accordance with the cadence of the pulses. Selection of the pulse sequence frequency, pitch and amplitude of the sound pulses are adjustable to enhance the process of falling asleep.

In U.S. Pat. No. 3,753,433, the use of audio tones and a binaural headset is disclosed. The headset is worn by a user and includes scalp electrodes that are placed on the head of the user when the headset is worn. The electrodes pick up brain wave signals which are converted to recognisable audio tones for the user so that the user can listen to his/her own brain waves.

WO-A-2006/101571 discloses a method that uses binaural beat for balancing the brain left side with the brain right side. An EEG system is used to measure the electrical signals produced by each side of the brain and an audio generator is used to generate the binaural beat to compensate for the imbalance.

In WO-A-00/16842, a digital sound relaxation system is disclosed in which sounds are used to mask ambient sounds and to induce a state of deep relaxation that helps the listener to fall asleep. Different modes are selectable by selecting a combination of mode select and sequential sound selector switches. An alarm mode is included that allows one or more sounds from a pre-recorded library to be used as the wake-up sound.

US-A-2009/105524 discloses a device for inducing sleep by playing music having a tempo of between sixty and eighty beats per minute to provide better sleep quality, better perceived sleep quality, longer sleep duration and greater sleep efficiency. The device may be provided in an alarm clock, a pillow, mobile, sleep mask, crib or a stuffed toy for use with children. The sleep-inducing device can also be made transportable for inducing better sleep during travel.

U.S. Pat. No. 3,884,218 discloses a method for inducing sleep in which familiar repetitive pleasing sounds are used, in combination with EEG signals, to induce various stages of sleep. The pleasing sounds are modulated by the EEG sleep signals. The pleasing sounds change in amplitude and frequency in accordance with the modulation of the EEG sleep signals. The audio signal is played continuously until a predetermined wake-up time in which they will stop allowing the individual to drift back to wakefulness.

By modulating the pleasing sounds with EEG sleep signals, they change in amplitude and frequency, and, such changes can disturb a user's sleep, particularly if large amplitude and frequency changes are experienced.

U.S. Pat. No. 5,135,468 discloses a method and apparatus for varying the brain state of a person in which first and second audio signals at respective first and second frequencies are provided to respective ears, the first and second audio frequencies varying in a range of approximately 0 to 60 Hz. In addition, the amplitude of each audio signal is varied so that the person perceives a constantly moving sound. Three embodiments are described in which a person can be relaxed, sent to sleep or energised in accordance with the type of binaural beat bands utilised.

WO-A-95/17854 discloses a trophotropic response system which aids a user in achieving a relaxation response. The system comprises a control unit and an audiovisual unit. The control unit includes a processor and associated hardware and software to control the audiovisual unit which comprises a light producing unit and a pair of headphones coupled thereto. Light from the light producing unit is directed onto a diffuser screen located between the eyes of a user and light sources located within the light producing unit. In this way, both light and sound are produced in response to control signals provided by the control unit to aid the user in performing a relaxation exercise. However, it would be impractical to use such a system as a sleep aid.

US-A-2008/0304691 discloses a sleep aid system in which speakers are enclosed in fabric to provide soft comfortable headphones that can be work as a sweatband or a watch cap when worn by a user. Binaural beat technology may be used where binaural beats are provided to the user via the sleep aid system. Alarm or wake-up functions may also be provided. However, a user of the system described in US-A-2008//0304691, needs to wear headphones when sleeping to be able to benefit from the use of the sleep aid.

WO-A-2008/131454 describes a sleep inducing and maintenance system in which binaural beat frequencies are used, the system comprising a soft fabric sleep mask into which are incorporated light-emitting diode (LED) elements and speakers. Coloured LED elements are matched to each binaural beat frequency and operate in synchronism with the binaural beat frequency. A binaural voice object is used to produce a binaural beat which plays a single part in a four part song, each part corresponding to one of alpha, beta, delta and theta brainwaves. Song files are disclosed which comprise a list of variable-length records ordered by time which are repeated until the particular session ends. Session files are used to adjust the intensity of the binaural beats with respect to time. A push button is used to index through sequences that relate to "go to sleep", "go back to sleep", "wake up" and "meditate", and another push button is used to start the chosen sequence.

It is therefore an object of the present invention to provide a device which promotes healthy, natural sleep patterns using binaural beat frequencies combined with either a background environmental sound which does not suffer from the problem of changes in amplitude and frequency of the environmental sound or a subliminal tone at a frequency that is not discernible to the user in the case where the user prefers a quiet room when sleeping.

SUMMARY OF THE INVENTION

In accordance with a first aspect of the present invention, there is provided a sleep inducing and sleep maintenance system comprising:—a housing; a control panel formed in the housing and allowing input information to be provided for selecting a sleep programme from a plurality of sleep programmes; a display formed in the housing for displaying information relating to at least a selected sleep programme; a memory located within the housing for storing parameters relating to the plurality of sleep programmes; a processing unit located within the housing for controlling the display and for processing input information received at the control panel relating to a selected sleep programme; and at least one pair of speaker units through which a selected sleep programme is relayed to a user; characterised in that the parameters stored in the memory comprise at least binaural beat frequencies used for each of the sleep programmes and loops of the binaural beat frequencies; and in that the processing unit is operable to retrieve the parameters from the memory and to compile the retrieved parameters into the selected sleep programme in accordance with the input information received from the control panel.

By storing the sleep programmes as parameters, each parameter can be selected in accordance with a selected sleep programme. This has the advantage that the memory need not store all programmes thereby saving memory space and providing flexibility of the system.

The parameters stored in the memory may further comprise a plurality of environmental sounds and loops of the environmental sounds.

In addition, the parameters stored in the memory may further comprise at least one of: a subliminal message sequence and an affirmative message sequence.

Preferably, each sleep programme comprises a sequence of binaural beat frequencies, each binaural beat frequency comprising a number of repeated loops arranged in accordance with a selected sleep programme. Each repeated loop may comprise a predetermined duration.

Advantageously, the plurality of sleep programmes comprises at least a deep sleep programme, and an alarm programme that comprises a deep sleep programme adjusted for an alarm time. The deep sleep programme each comprises binaural beats in the alpha, delta and theta frequency bands.

The term "deep sleep programme" as used herein refers to a sleep programme that guides a user through the natural sleep patterns over a period of eight hours using an appropriate sequence of binaural beat frequencies.

Each sleep programme may further include at least one of a subliminal message sequence and an affirmative message sequence running at the same time as the sequence of binaural beat frequencies for a portion of the sleep programme. At least one of the subliminal message sequence and the affirmative message sequence may be used at the start of the sleep programme. Alternatively, or in addition, at least one of the subliminal message sequence and the affirmative message sequence may be used at the end of the sleep programme.

Advantageously, each sleep programme further comprises a wake-up sequence in at least the beta frequency band.

A power nap programme may also be included that comprises one of: a 15-minute programme; a 30-minute programme; a 45-minute programme; and a 60-minute programme. Binaural beat frequencies in at least the alpha 01 and alpha 02 frequency bands may be used together with a wake-up sequence in the beta frequency band.

The term "power nap programme" as used herein refers to a sleep programme in which a user is guided through a short period of sleep using an appropriate sequence of binaural beat frequencies.

For longer power nap programmes, namely, the 30-, 45- and 60-minute programmes, binaural beats in the alpha 03 frequency band may also be used. In addition, each of the longer power nap programmes may further include at least one of a subliminal message sequence and an affirmative message sequence running at the same time as the sequence of binaural beat frequencies for a portion of the power nap programme. In this case, each of the subliminal message sequence and the affirmative message sequence are used at the start of the power nap programme.

In addition, a falling asleep programme may be provided. Such a programme allows a user to fall asleep as it only runs for a relatively short period of time. The falling asleep programme may comprise binaural beats in the alpha, delta and theta frequency bands.

In one embodiment, at least one sleep programme for children is provided. In another embodiment, a jet lag sleep programme is provided.

Preferably, a selected environmental sound is played for the duration of the selected sleep programme.

The term "environmental sound" as used herein is intended to include background sounds as well as a subliminal tone, that is, no discernible noise or sound, for users who prefer a quiet room with no sound when sleeping.

By combining the selected environmental sound with at least binaural beat frequencies, no modulation is required to the environmental sound and it remains at a constant amplitude and frequency. This constant amplitude and frequency does not disturb a user's sleep.

At least one pair of speaker units may be formed in the housing. Additionally or alternatively, at least one pair of speaker units may be separated from the housing and connected thereto to receive signals corresponding to the selected sleep programme.

In accordance with another aspect of the present invention, there is provided a method for inducing and maintaining sleep using a system as described above, the method comprising the steps of:—a) selecting a sleep programme; and b) compiling the selected sleep programme, the selected sleep programme comprising at least a sequence of binaural beat frequencies corresponding thereto.

Preferably, step a) further comprises selecting an environmental sound, and step b) comprises compiling the sequence of binaural beat frequencies with the environmental sound.

In accordance with yet another aspect of the present invention, there is provided a method for inducing and maintaining sleep in an individual, the method comprising the steps of:—a) selecting a sleep programme; b) determining a sequence of binaural beat frequencies in accordance with the selected sleep programme; determining a number of loops for each binaural beat frequency in the sequence of binaural beat frequencies; d) compiling the sequence of binaural beat frequencies into the selected environmental sound, each binaural beat frequency being run for a predetermined number of loops in accordance with the selected sleep programme to provide a sleep cycle; and e) exposing the individual to the sleep cycle.

The term "loop" as used herein refers to a predetermined duration for which each binaural beat frequency is run. In addition, the term "loop" may also refer to the duration of a segment of an environmental sound, each segment being run a predetermined number of times in accordance with a selected sleep programme.

The method may further comprise the step of selecting an environmental sound, and step d) comprises compiling the sequence of binaural beat frequencies with the environmental sound for the entire duration of the selected sleep programme.

In accordance with a further aspect of the present invention, there is provided a method of compiling a sleep programme for an individual, the method comprising the steps of:—a) selecting a sequence of binaural beat frequencies in accordance with a selected sleep programme; b) determining a number of loops for each binaural beat frequency in the sequence of binaural beat frequencies; and c) compiling the sequence of binaural beat frequencies in accordance with the selected sleep programme, each binaural beat frequency in the sequence of binaural beat frequencies running for the determined number of loops.

Preferably, step c) may comprise compiling the sequence of binaural beat frequencies with a selected environmental sound, the environmental sound running simultaneously with the sequence of binaural beat frequencies.

Step c) may comprise adjusting the sequence of binaural beat frequencies in accordance with a predefined wake-up time. Alternatively or additionally, step c) may comprise adjusting the number of loops for each binaural beat frequency in the sequence of binaural beat frequencies in accordance with a predefined wake-up time.

Step c) may further comprise adding at least one subliminal message sequence. Alternatively or additionally, step c) may further comprise adding at least one affirmative message sequence.

In accordance with a yet further aspect of the present invention, there is provided a computer program for executing the method as described above, using a computerised system.

BRIEF DESCRIPTION OF THE DRAWINGS

For a better understanding of the present invention, reference will now be made, by way of example only, to the accompanying drawings in which:—

DESCRIPTION OF THE INVENTION

The present invention will be described with respect to particular embodiments and with reference to certain drawings but the invention is not limited thereto. The drawings described are only schematic and are non-limiting.

When awake, brain wave patterns for most people can be categorised into two types of waves, namely, beta waves and alpha waves. Beta waves are associated with wakefulness and are highest in frequency and lowest in amplitude. In addition, beta waves have no consistent pattern due to normal day-to-day mental activity and can be considered to be de-synchronous. During periods of relaxation whilst still awake, brain waves become slower, increase in amplitude and become more synchronous. These brain waves are the alpha waves and have a frequency of between 8 to 13 Hz approximately.

Sleep has various stages and during a normal night's sleep an individual passes between the stages. The first and second stages of sleep are considered to be relatively "light" stages of sleep and a person may not even realise that they are asleep. The first stage of sleep is defined by the presence of theta wave activity in the brain. Theta waves, typically having a frequency of between 4 and 7 Hz are slower and have higher amplitudes than alpha waves. The second stage of sleep also comprises theta waves but is interspersed by what are termed as sleep spindles and K complexes. Sleep spindles occur due to a sudden increase in wave frequency (between 11 to 16 Hz and more typically between 12 and 14 Hz), and K complexes occur due to a sudden increase in wave amplitude.

During the third and fourth stages of sleep, theta waves are replaced by delta waves. Delta waves are the slowest and highest amplitude brain waves, typically having frequencies of between 0.5 to 2 Hz. The third stage and fourth stage, which can be considered to be a single stage, are defined by the amount of delta waves present in wave activity of the brain—in the third stage, there are less than 50% delta waves, and in the fourth stage, there are more than 50% delta waves. Delta sleep is the deepest sleep and it is often difficult to wake sleepers from this type of sleep. When awoken from delta sleep, individuals are usually sleepy and disoriented. Sleep walking and sleep talking are most likely to occur in delta sleep.

In addition to the stages of sleep described above, there is also rapid eye movement (REM) sleep. In REM sleep, brain waves show a combination of alpha, beta and de-synchronous waves. REM sleep is the stage of sleep that is most associated with dreaming and is similar to being awake in terms of brain activity. Infants spend almost 50% of their time in REM sleep but adults spend almost 50% of their sleep time in the second stage with about 20% in REM and the other 30% divided between the other three stages.

Usually, sleepers pass through all five stages which tend to progress cyclically from the first stage through to the REM stage and then restarts with the first stage. A complete sleep cycle takes an average of 90 to 110 minutes. The first sleep cycles tend to have relatively short REM sleep and long periods of deep sleep but later in the night, REM sleep periods lengthen and deep sleep time decreases.

The present invention utilises binaural beat frequencies frequencies to guide a user through sleep cycles. Binaural beat frequencies are created by a difference in frequency between two tones played to the user, for example, if one tone has a frequency of 300 Hz and the other tone has a frequency of 310 Hz, the binaural beat is 10 Hz. The user experiences a beating tone as if the two tones are mixed naturally out of the brain and the frequencies of the tones must be below 1 kHz with a difference between the two tones of at least 30 Hz for the beating effect to be noticeable.

Binaural beat frequencies are combined with an environmental sound to induce and maintain sleep, the binaural beat frequencies and the environmental sound running simultaneously through the entire sleep programme. Additionally, a subliminal or affirmative message sequence may also be added at the start of the sleep programme and/or at the end of the sleep programme extending into a wake-up sequence. If a subliminal and/or affirmative message sequence is added, it runs simultaneously with an appropriate part of the sleep programme, for example, if such messages are to be run at the end of the sleep programme, they are timed to start at a point within the sleep programme that allows them to end at the same time as the sleep programme.

The system in accordance with the present invention cycles through the stages of sleep described above to provide a natural healthy sleep pattern. The system provides eight background environmental sounds which have been established using binaural beat technology to support each stage of the sleep cycle. These background environmental sounds include four nature environments (ocean, rain, river and wind), one rhythmic environment (train) and three 'cocoon' environments for masking external noise (low pitch, medium pitch and high pitch).

It will be appreciated that, although eight background environmental sounds are provided in the device according to the present invention, any suitable number of background environmental sounds can be provided. Moreover, for users that prefer quiet when they sleep, instead of selecting a background environmental sound, it is also possible to select an environment sound which comprises a subliminal tone outside the range of human hearing providing no discernible sound or noise. Such a subliminal tone operates with the same binaural beat patterns as those used with background environmental sounds. Such tones may operate in the range of 10.5 to 18 kHz, preferably 12 to 18 kHz, more preferably, 12 to 14 kHz.

In addition, four main sleep programs are provided in the system to meet the needs of an individual: a deep sleep programme in which individuals are taken through all five sleep stages over a period of 8 hours; an easy sleep or alarm programme which adjusts the deep sleep programme for a particular wake-up time; a fall asleep programme which runs for around 90 minutes enabling the individual to fall asleep; and power nap programme where short sleep periods are induced. Each of the deep sleep, alarm and power nap programmes also include a wake-up sequence.

Subliminal or affirmative message sequences can also be added to each of the programmes provided they are not too short. For example, in the case of the 15-minute power nap programme, no subliminal or affirmative message sequences can be incorporated due to its short duration. Such sequences can be incorporated at the start and/or at the end of the programme. If the sequence is incorporated at the end of the programme, it usually starts before the wake-up sequence begins and may have a different duration to a subliminal or affirmative message sequence at the start of the programme.

Figure 1:
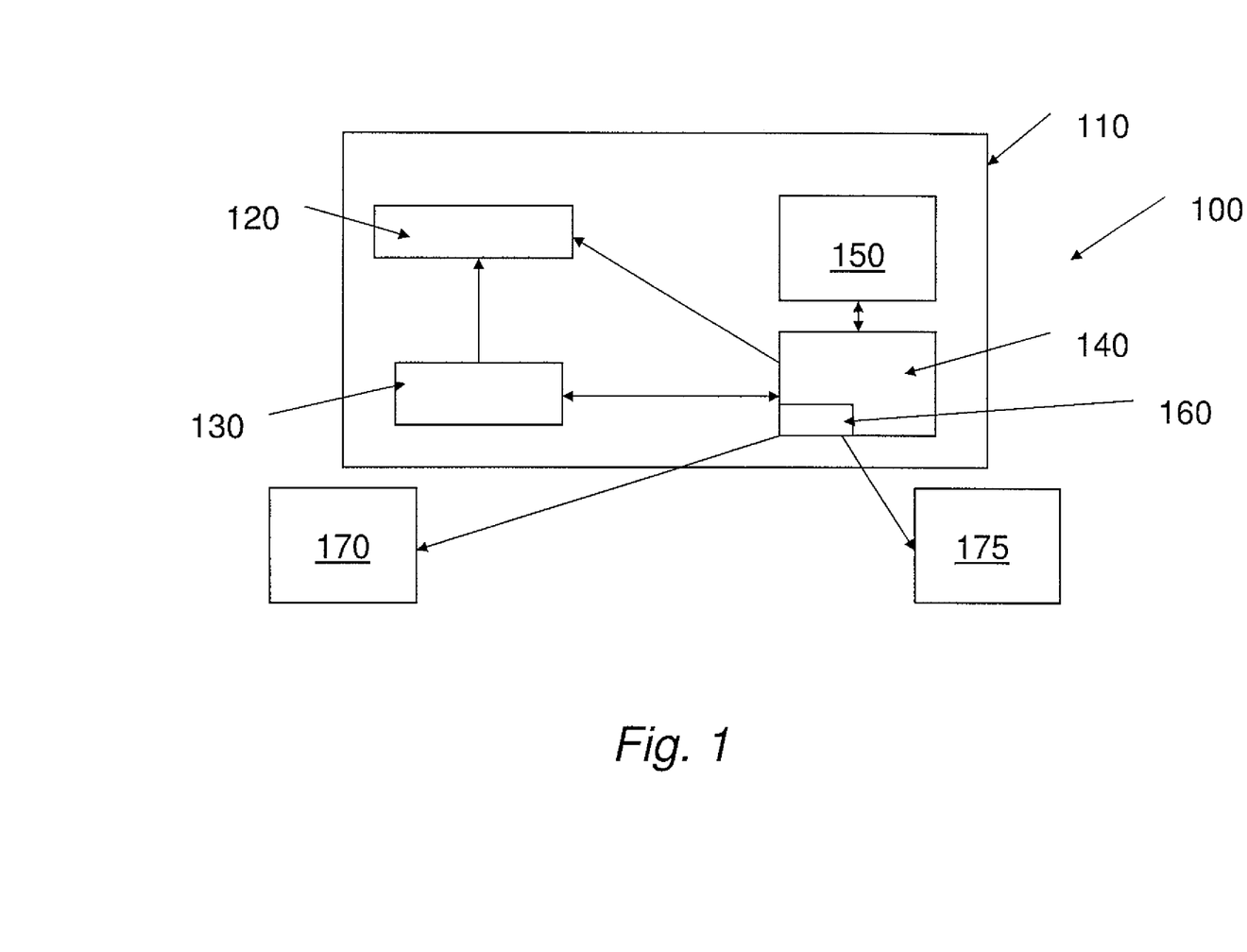
FIG. 1 illustrates a schematic arrangement of a device in accordance with the present invention.

A sleep inducing and sleep maintenance system 100 in accordance with the present invention is shown in FIG. 1. The system 100 comprises a housing 110 having a display 120 and a control panel 130. The system 100 also includes a processing unit 140 and a memory 150. The processing unit 140 includes a driver 160 for a pair of speaker units 170, 175 as shown.

The display 120 displays information relating to the time and the programme selected. It can also display an alarm function as will be readily understood. The control panel 130 includes means (not shown) for selecting sleep programmes, setting the time, setting an alarm, controlling the volume etc.

The processing unit 140 controls the operation of the system 100 and is connected to the display 120, the control panel 130, the memory 150 and the speaker units 170, 175 by means of the driver 160.

In the memory 150, the sleep programmes as described above are stored. When a particular programme is to be used, the user selects the programme using the control panel 130 and can see his/her selection on the display 120. The selected programme is retrieved from the memory 150 and run by the processing unit 140. Audio signals produced by the processing unit 140 are passed to the driver 160 which transmits the signals to the speaker units 170, 175.

It will be appreciated that the memory 150 may form part of the processing unit 140 and is only shown here for ease of explanation. It will also be appreciated that the display 120 and control panel 130 are controlled by the processing unit 140.

It will also be appreciated that although two separate speaker units are shown in FIG. 1, a single speaker unit may be provided which can be located remotely from the housing 110 with a speaker unit being integrally formed with the housing. Connections to each speaker unit can be wired or can be wireless using known wireless technologies.

In a preferred embodiment, the sleep programmes are stored as components or parameters within the memory 150, that is, the binaural beat frequencies used for the sleep programmes as will be described in more detail below, the number of loops for each binaural beat frequency and their duration as will be described in more detail below, the subliminal message sequences and their duration, the affirmative message sequences and their duration, the environmental sounds as described above and their duration, and the sequences of binaural beat frequencies for each sleep programme.

When a sleep programme is selected by a user of the system 100, the processing unit 140 compiles the selected sleep programme from the components or parameters. By storing components or parameters of each sleep programme, less memory is required as each sleep programme is compiled as required. In addition, a more flexible system is provided which can be adjusted for different and/or additional sleep programmes that can be added to the system.

Each sleep programme provided by the system 100 will now be described in more detail below with reference to FIGS. 2 to 8. It is to be appreciated that these sleep programmes are by way of example only and that other sleep programmes may be possible. The sleep programmes to be described below include a deep sleep programme, an easy sleep programme, a fall asleep programme and power nap programmes.

The term "deep sleep programme" as used herein refers to a sleep programme that guides a user through the natural sleep patterns over a period of eight hours using an appropriate sequence of binaural beat frequencies.

The term "power nap programme" as used herein refers to a sleep programme in which a user is guided through a short period of sleep using an appropriate sequence of binaural beat frequencies.

Figure 2:
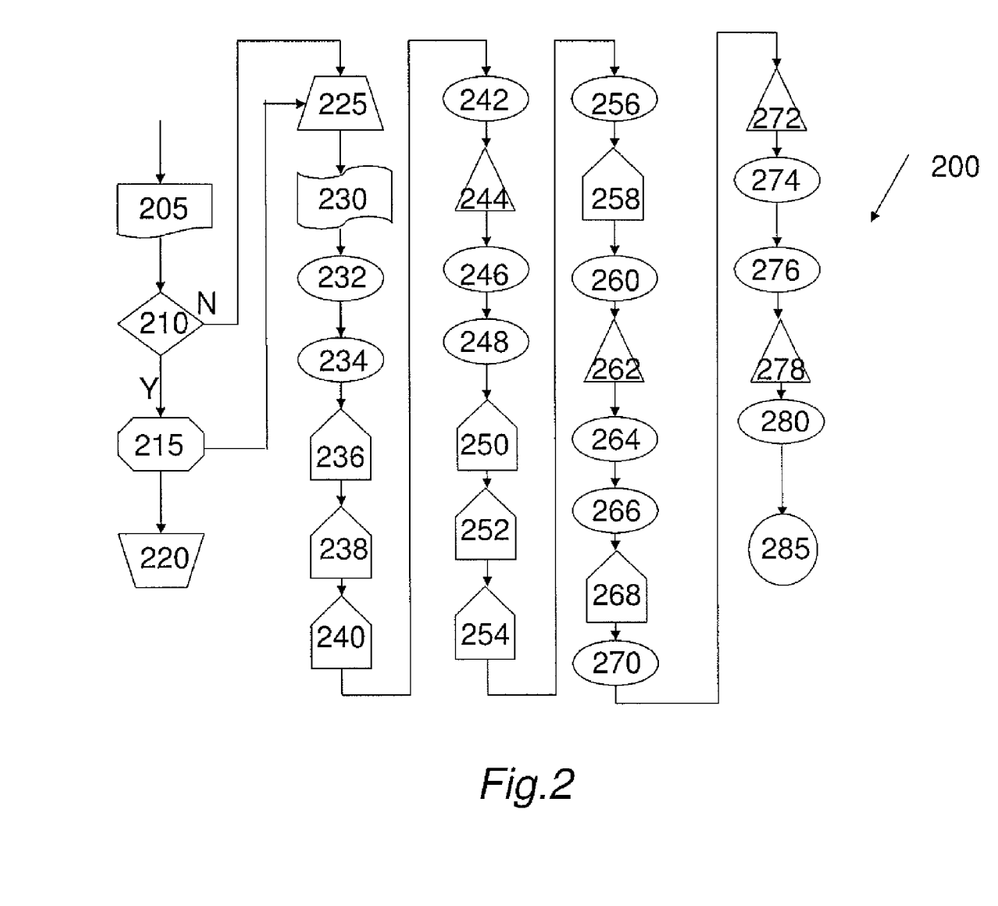
FIG. 2 illustrates a flow chart of a deep sleep programme in accordance with the present invention.

In FIG. 2, a flow chart 200 for the deep sleep programme is shown. Over 8 hours, what is considered to be a good night's sleep, the programme takes a user of the device through all stages of sleep ensuring that the five REM cycles are experienced.

Having selected the deep sleep programme, the user first selects one of the eight sound environments which he would like to use. As mentioned above, these environments include sounds relating to ocean, rain, river, wind (nature), train (rhythmic), brown (low pitch), pink (medium pitch) and white (high pitch). The last three environments relate to 'cocoon' environments and mask external noise. Alternatively, a subliminal tone which provides no discernible sound can be selected in the case where the user prefers not to have any sound. These environmental sounds are played at the same time as the binaural beat frequencies as will be described in more detail below.

The user may also select whether to receive a subliminal or affirmative message sequence as part of the programme (step 210). If the user selects to receive a subliminal or affirmative message sequence, the message sequence is fed into the deep sleep programme at step 225 (described in more detail below) and is played for 12 loops (step 215) at the same time as the chosen environmental sound and the loops corresponding to the particular portion of the sleep sequence. Here, each loop in the subliminal or affirmative message sequence lasts for approximately 5 minutes, and for the start of the sleep programme the subliminal or affirmative message sequence lasts for a period of 60 minutes. After the subliminal or affirmative message sequence has been played, the sound fades down (step 220). Naturally, if the user selects not to receive a subliminal or affirmative message sequence, step 210 leads directly to fade up, step 225.

Each environmental sound loop lasts for approximately 7.5 minutes and each loop in the sequence of binaural beat frequencies lasts approximately 1 minute. Only the subliminal or affirmative message sequence loops are approximately 5 minutes long. The values for the duration of loops of the environmental sound and the subliminal or affirmative message sequence are given by way of example and may be of any suitable duration in accordance with the particular application of the present invention. However, it will be appreciated that the duration of each loop of the sequence of binaural beat frequencies and the environmental sound loops need to be chosen so that they can run together.

In addition, each binaural beat band used has a defined frequency range and these are referred to as alpha 01 (between 9 to 10 Hz), alpha 02 (between 8 and 8.9 Hz), alpha 03 (between 7.1 and 7.9 Hz), theta 01 (between 6.1 and 7 Hz), theta 02 (between 4 and 4.9 Hz), delta (between 1 and 1.9 Hz) and beta (between 12 and 16 Hz). However, it will be appreciated that these ranges are also given by way of example only, and that other suitable frequency ranges can be used within each of the alpha (between 7 and 13 Hz), theta (between 4 and 7 Hz), delta (less than 4 Hz) and beta (between 13 and 39 Hz) bands. Each binaural beat frequency is carried on a carrier signal having a frequency of around 110 Hz. Naturally, any other suitable carrier signal can be used, for example, harmonics of 110 Hz such as 220 Hz and 330 Hz.

After fade up in step 225, the selected environmental sound is played for 64 loops (step 230). During these loops, the environmental sound is played at the same time as the binaural beat frequency for that particular part of the programme. As described above, the environmental sound is played throughout the deep sleep programme. The binaural beat sequence for the deep sleep programme comprises alpha loops, theta loops and delta loops arranged for the five stages of sleep followed by a wake-up sequence of beta loops.

In a particular embodiment of the invention, the deep sleep programme sequence comprises two sets of alpha loops (steps 232 and 234), three sets of theta loops (steps 236, 238 and 240), one set of an alpha loop (step 242), one set of a delta loop (step 244), two sets of alpha loops (steps 246 and 248), three sets of theta loops (steps 250, 252 and 254), one set of alpha loops (step 256), one set of theta loops (step 258), one set of alpha loops (step 260), one set of delta loops (step 262), two sets of alpha loops (steps 264 and 266), one set of theta loops (step 268), one set of alpha loops (step 270), one set of delta loops (step 272), two sets of alpha loops (steps 274 and 276), one set of delta loops (step 178), one set of alpha loops (step 280) and a wake-up sequence (step 285). The particular frequencies and number of loops played are given in Table 1 below. However, the frequencies and loops illustrated are not limiting and the frequencies and the loops can be varied independently without departing from the present invention. For example, the frequencies and/or loops can be varied for children with different frequencies and/or loops being used for different age groups. In one embodiment of the present invention, six deep sleep programmes may be provided where one is for adults, as described above with reference to FIG. 2, and the other five are for children between 2 and 12 months old, between 1 and 3 years old, between 3 and 5 years old, between 6 and 12 years old, and between 13 and 18 years old. Naturally, the choice of the deep sleep programmes for children may depend on the development of the child, particularly around the top of one age range and the bottom of the next age range.

TABLE 1

| Step No. | Binaural Beat | No. of Loops |
| --- | --- | --- |
| 232 | Alpha 01 | 12 |
| 234 | Alpha 02 | 12 |
| 236 | Theta 01 | 12 |
| 238 | Theta 02 | 36 |
| 240 | Theta 01 | 12 |
| 242 | Alpha 03 | 6 |
| 244 | Delta | 30 |
| 246 | Alpha 02 | 6 |
| 248 | Alpha 03 | 12 |
| 250 | Theta 01 | 12 |
| 252 | Theta 02 | 12 |
| 254 | Theta 01 | 12 |
| 256 | Alpha 03 | 12 |
| 258 | Theta 01 | 6 |
| 260 | Alpha 03 | 18 |
| 262 | Delta | 42 |
| 264 | Alpha 02 | 6 |
| 266 | Alpha 03 | 24 |
| 268 | Theta 01 | 6 |
| 270 | Alpha 02 | 18 |
| 272 | Delta | 60 |
| 274 | Alpha 02 | 12 |
| 276 | Alpha 03 | 30 |
| 278 | Delta | 48 |
| 280 | Alpha 02 | 12 |

After 60 minutes, the subliminal or affirmative message sequence, if selected, will also fade out in step 220 as described above and leaving the deep sleep programme and the selected environmental sound.

Once step 280 has been attained, the user has had approximately 8 hours sleep and it is almost time for he/she to be woken up. A wake-up sequence, shown as step 285, comprises 18 loops of beta. The user is now awake.

If a subliminal or affirmative message sequence has been selected for wake-up (not shown), it runs for 90 minutes (18 loops of 5 minutes) at the same time as the end of the deep sleep programme through to the end of the wake-up sequence (step 285). As described above the subliminal or affirmative message sequence comprises loops of 5 minutes. This means that the subliminal or affirmative message sequence for wake-up starts with step 274 having faded up during the set of delta loops in step 272 so that it ends with the end of the beta loops in the normal wake-up sequence.

In the described embodiment of the deep sleep programme, there are two different subliminal or affirmative message sequences are used, one for use at the start of the deep sleep programme and one for the wake-up sequence.

It will be appreciated that the user is free to select the use of subliminal or affirmative message sequences and may use them at the start of the programme and/or before and during the wake-up sequence. Each subliminal or affirmative message sequence may be pre-recorded using an alpha-female voice.

Although specific frequencies can be used for each band, other specific frequencies can be chosen provided they are within the desired band. Additionally, the number of loops in each step may be varied if required. An example of where the number of loops needs to be varied is when an alarm is required as shown in FIG. 3.

Figure 3:
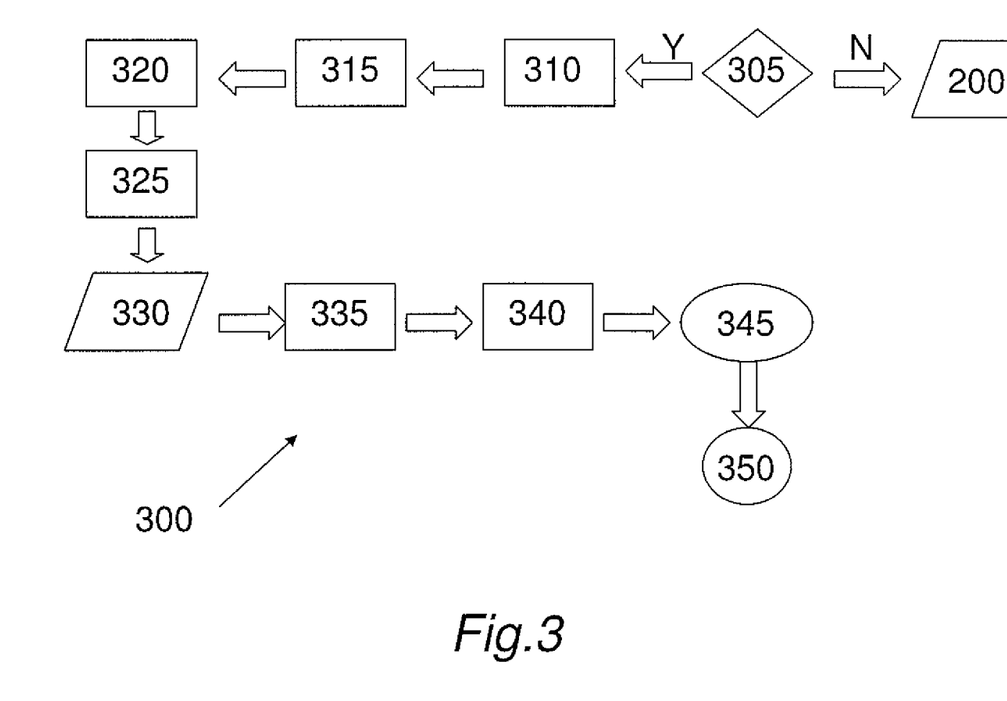
FIG. 3 illustrates a flow chart of an easy sleep programme in accordance with the present invention.

In FIG. 3, a flow chart 300 is shown in which the system 100 (FIG. 1) is set as an alarm clock. In this case, the system 100 runs an easy sleep programme comprising a modified deep sleep programme provided the alarm is set for less than 8 hours from the current time. The first step in the flow chart 300 is to determine whether an alarm has been set or not (step 305). If an alarm has not been set, the deep sleep programme can be run as indicated by step 200 (corresponding to flow chart 200 as described above with reference to FIG. 2). If an alarm has been set, some calculations need to be carried out to re-time the deep sleep programme for the available time. The first step is to determine the current time. This is read from the system 100 (FIG. 1) in step 310. The alarm time, step 315, is also determined from the system 100 and the difference between the current time and the alarm time is calculated in minutes (step 320). Time is then subtracted for the wake-up sequence in step 325, that is, 18 minutes is subtracted, to provide the 'programme time' in step 330. The deep sleep programme is then run for the 'programme time' in step 335. At the end of the 'programme time' (step 340), the wake-up sequence is run as shown by steps 345 and 350. Steps 345 and 350 comprise respectively 6 loops of alpha 02 and 12 loops of beta.

It is to be noted that, if the alarm time is set for more than eight hours from the current time, only the deep sleep programme will run with or without subliminal and/or affirmative message sequences as desired by the user. However, in other embodiments, it may be possible to extend the wake-up sequence to allow for differences in timing although that is not the case in the present embodiment of the easy sleep programme.

It will be appreciated that there are several ways in which the deep sleep programme can be adjusted for the alarm time. Examples of how this adjustment can be implemented include but are not limited to: running the deep sleep programme from the start and terminating it at the end of the 'programme time'; adjusting each set of loops throughout the entire programme; adjusting the frequency bands for at least some of the loops; and modifying the deep sleep programme to ensure that the important parts of the sleep cycle are experienced by the user, for example, REM periods 1, 4 and 5 with REM periods 2 and 3 being removed. However, the amount of adjustment required will depend on the 'programme time' available. In a preferred embodiment described above in which components or parameters of the sleep programmes are stored in the memory 150 and compiled by the processing unit 140 when required, changes to the duration of the deep sleep programme can readily be implemented when an alarm is used.

If the selection has been made for a subliminal message sequence or an affirmative message sequence to be run at the end of the easy sleep programme, this message sequence is run at the same time as the end of the reduced deep sleep programme and the wake-up sequence. Here, as the 'programme time' for the deep sleep programme is varied in accordance with the difference between the alarm time and the current time less the wake-up sequence, the subliminal or affirmative message sequence will start at an appropriate time during the reduced deep sleep programme to provide a subliminal or affirmative message sequence having a duration of 90 minutes.

Although not shown in FIG. 3, the re-timed deep sleep programmed may also include a subliminal or affirmative message sequence at the start of the programme as described above with reference to FIG. 2. Naturally, it will be appreciated that if the alarm time is too close to the current time, there may not be sufficient time to run a subliminal or affirmative message sequence both at the start of the programme and also at the end of the programme, for example, if the difference between the alarm time and the current time is less than 150 minutes. As an alternative, different subliminal or affirmative message sequences may be provided for use with the alarm mode, each message sequence having suitably shorter durations. In a preferred embodiment described above in which components or parameters of the sleep programmes are stored in the memory 150 and compiled by the processing unit 140 when required, changes to the duration of the subliminal and/or affirmative message sequences can readily be implemented when an alarm is used. As described above with reference to FIG. 2, the subliminal or affirmative message sequence used for wake-up can be the same or different to the subliminal or affirmative message sequence used at the start of the programme depending on the particular embodiment.

The embodiments of the sleep programmes described above with reference to FIGS. 2 and 3 are intended for users who cannot have a good night's sleep for whatever reason. If a user only requires help getting to sleep, a shorter programme can be used, for example, a fall asleep programme having a 90-minute duration.

Figure 4:
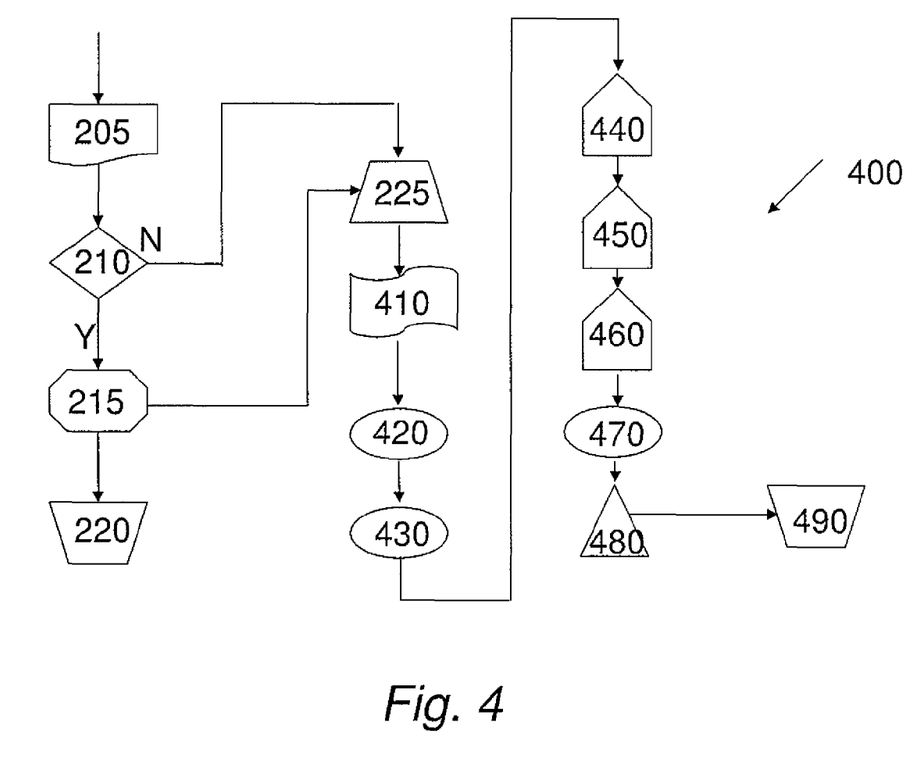
FIG. 4 illustrates a fall asleep programme in accordance with the present invention.

A 90-minute sleep programme is indicated by flow chart 400 in FIG. 4. Here, the steps up to and including fade up, step 225, are the same as those described above with reference to FIG. 2. Steps that have previously been described are reference the same and are not described again here in detail. From step 255, the fade up step, the selected environmental sound is played for 12 loops of 7.5 minutes (step 410) and as described above lasts for the full duration of the 90-minute sleep programme. At the same time, two sets of alpha loops (steps 420 and 430), three sets of theta loops (steps 440, 450 and 460), one set of alpha loops (step 470) and one set of delta loops (step 480) are played and followed by a 90 second fade out in step 490. After the fade out step, the system 100 turns off leaving the user to sleep unaided.

In this sleep programme, a subliminal or affirmative message sequence can only be played at the start, if required, as there is no wake-up sequence.

Possible binaural beat frequencies and the number of loops for the sleep programme described with reference to FIG. 4 are given in Table 2 below.

TABLE 2

| Step No. | Binaural band | No. of loops |
| --- | --- | --- |
| 420 | Alpha 01 | 9 |
| 430 | Alpha 02 | 9 |
| 440 | Theta 01 | 12 |
| 450 | Theta 02 | 12 |
| 460 | Theta 01 | 12 |
| 470 | Alpha 03 | 6 |
| 480 | Delta | 30 |

In addition to wishing to obtain a good night's sleep with or without an alarm or needing help to fall asleep, the device can be used for "power napping" where a user sleeps for a predetermined amount of time and is then woken up to be refreshed and ready to carry on with his/her normal activities.

Figure 5:
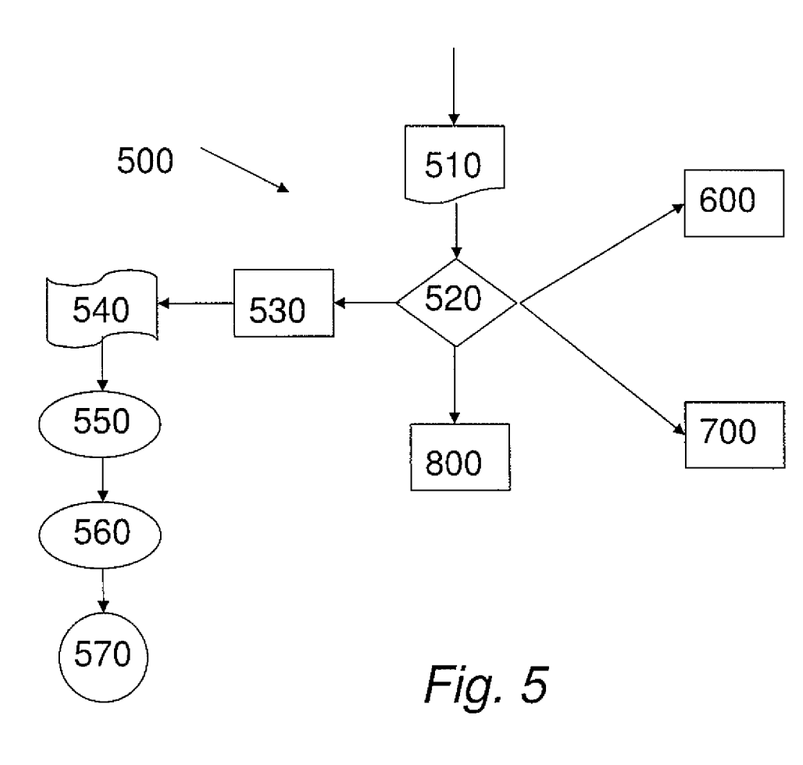
FIG. 5 illustrates a flow chart of a power nap programme in accordance with the present invention in which different times can be selected.

FIG. 5 illustrates a flow chart 500 for a power nap programme. The flow chart 500 is generalised for three of the four power nap options with the 15-minute power nap flow chart being shown in full. The 30-minute, 45-minute and 60-minute power nap flow charts are shown in more detail in FIGS. 6, 7 and 8 respectively. Whilst a subliminal or affirmative message sequence can be included for the 30-, 45- and 60-minute programmes, there is no subliminal or affirmative message sequence for wake-up due to the short duration of the power nap programmes.

In FIG. 5, having selected the environmental sound for the power nap programme, step 510, the user then selects one of the four time options, namely, 15 minutes, 30 minutes, 45 minutes, and 60 minutes, in step 520. The 30-, 45-, and 60-minute power nap options are indicated by steps 600, 700, 800 and the 15-minute power nap option starts with step 530. In step 540, 2 loops of the chosen environmental sound is played for 15 minutes (2 loops of 7.5 minutes) together with 6 loops of alpha 01 (step 550). Step 550 is followed by 6 loops of alpha 02 (step 560) and then a wake-up sequence (step 570) comprising 3 loops of beta. Because the 15-minute power nap programme is so short, there is no possibility of selecting a subliminal or affirmative message sequence as part of this programme.

Figure 6:
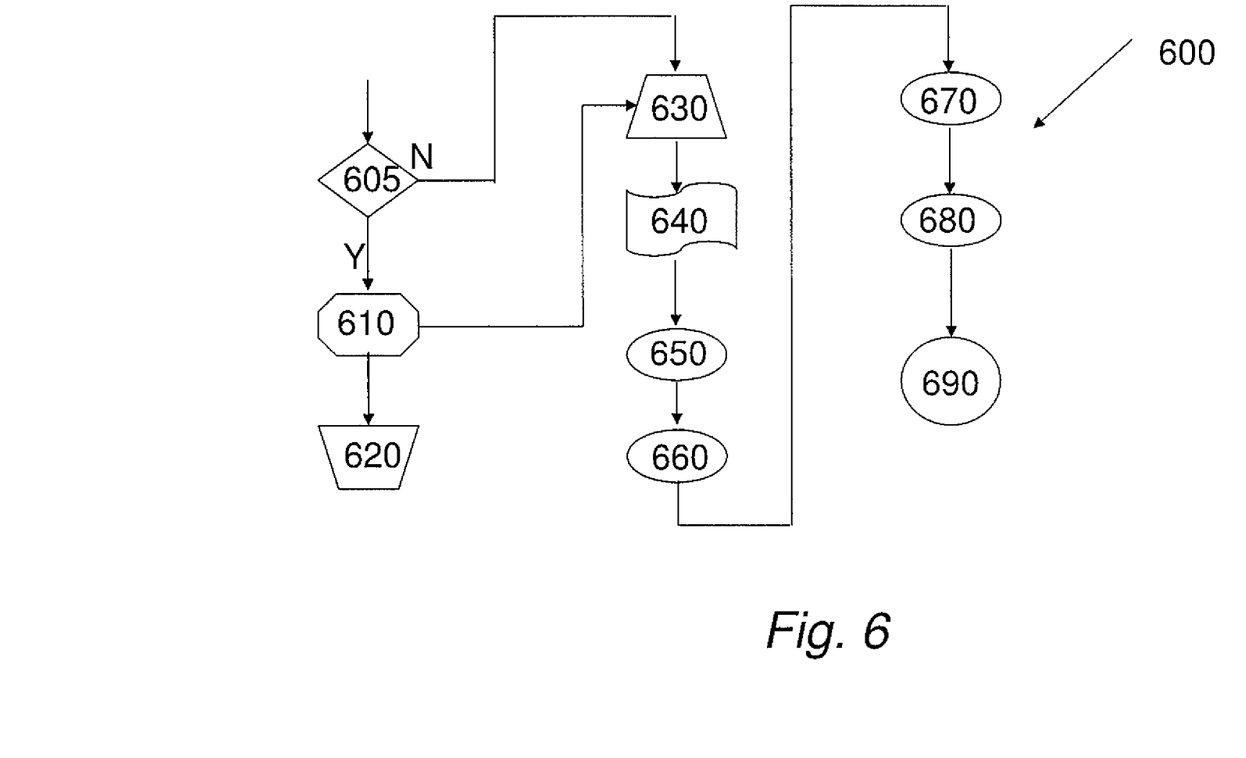
FIG. 6 illustrates a flow chart for a 30-minute power nap programme.

The flow chart 600 shown in FIG. 6 illustrates the steps of the 30-minute power nap programme in more detail. In step 605, a determination is made whether a subliminal or affirmative message sequence has been selected. If a subliminal or affirmative message sequence is to be played, this message sequence is played at the same time as the 30-minute power nap programme and comprises 6 loops of 5 minutes (step 610) and therefore runs for the whole of the 30-minute power nap programme. The subliminal or affirmative message sequence is played at the same time as the 30-minute power nap programme before fade down (step 620). If no subliminal or affirmative messages are to be played, the programme starts at step 630. In step 630, there is fade up before 4 loops of 7.5 minutes each of the selected environmental sound being played (step 740) at the same time as the programme. Here, the programme comprises 6 loops each of alpha 01 (step 750), alpha 02 (step 760), alpha 03 (step 770), and alpha 02 (step 780). The programme ends with a wake-up sequence (step 790) comprising 6 loops of beta.

Figure 7:
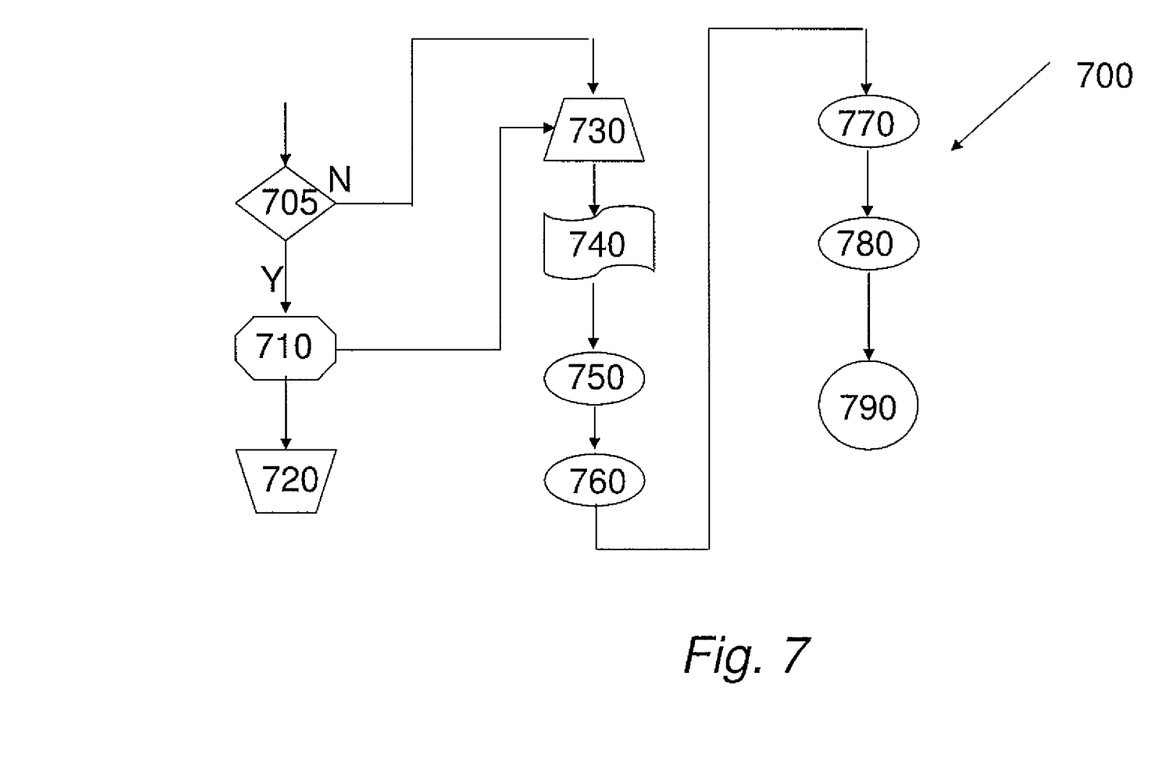
FIG. 7 is similar to FIG. 6 but illustrates a flow chart for a 45-minute power nap programme.

FIG. 7 is similar to FIG. 6 in that the flow chart 700 for the 45-minute power nap programme has the same steps as the 30-minute power nap programme but has a different numbers of loops. In step 705, a determination is made whether a subliminal or affirmative message sequence has been selected. If a subliminal or affirmative message sequence is to be played, 9 loops of these messages are played (step 710) followed by a fade down (step 720). As before, the 9 loops of the subliminal or affirmative message sequence are played at the same time as the 45-minute power nap programme starting at step 730. If no subliminal or affirmative message sequence is to be played, the programme starts at step 730. In step 730, there is fade up before 6 loops of the selected environmental sound is played (step 740) at the same time as 6 loops of alpha 01 (step 750), 6 loops of alpha 02 (step 760), 12 loops of alpha 03 (step 770), and 6 loops of alpha 02 (step 780) are played. The programme ends with a wake-up sequence (step 790) comprising 15 loops of beta.

Figure 8:
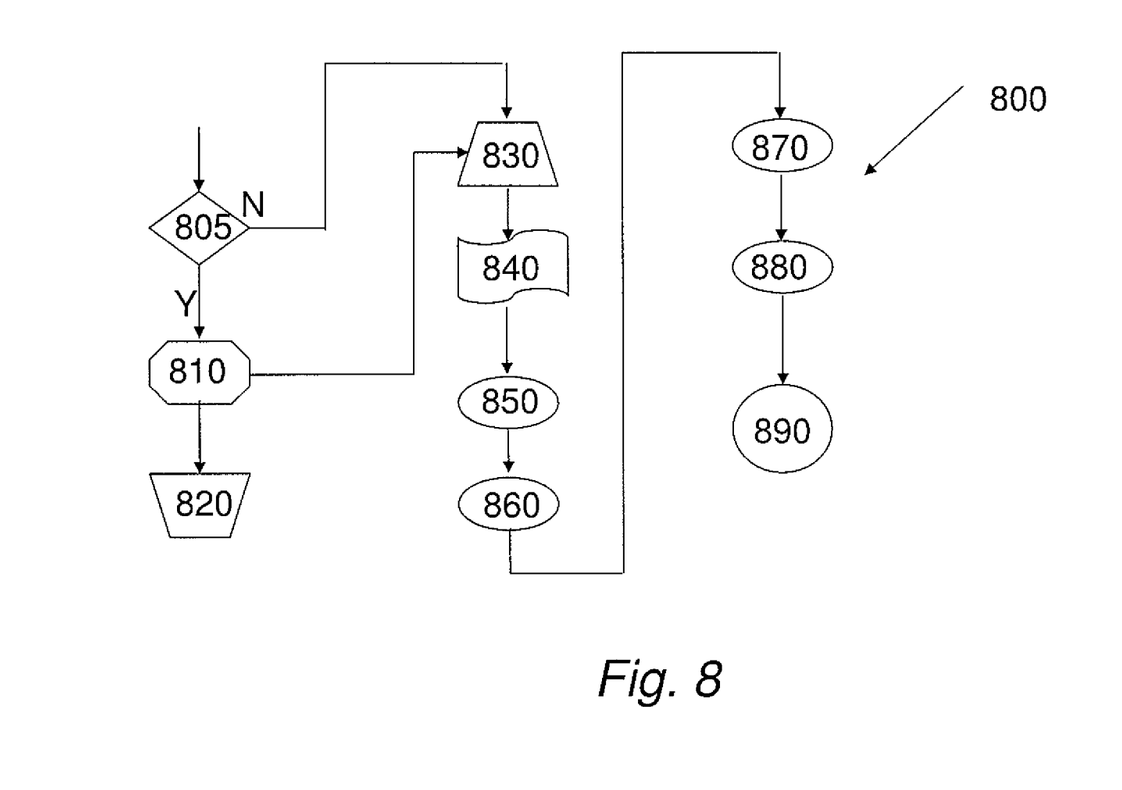
FIG. 8 is similar to FIGS. 6 and 7 but illustrates a flow chart for a 60-minute power nap programme.

FIG. 8 is similar to FIG. 6 in that the flow chart 800 for the 60-minute power nap programme has the same steps as the 30-minute power nap programme but has a different numbers of loops. In step 805, a determination is made whether a subliminal or affirmative messages sequence has been selected. If a subliminal or affirmative message sequence is to be played, 12 loops of these messages are played (step 810) followed by a fade down (step 820). As before, the 12 loops of the subliminal or affirmative message sequence are played at the same time as the 60-minute power nap programme starting at step 830. If no subliminal or affirmative message sequence is to be played, the programme starts at step 830. In step 830, there is fade up before 8 loops of the selected environmental sound are played (step 840) together with 12 loops of alpha 01 (step 850), 12 loops of alpha 02 (step 860), 12 loops of alpha 03 (step 870), and 12 loops of alpha 02 (step 880). The programme ends with a wake-up sequence (step 890) comprising 12 loops of beta.

It will be appreciated that, although the present invention has been described to operate with subliminal or affirmative message sequences running at the same time as the environmental sounds and the sleep programme, in some embodiments, it may be desirable to run the subliminal or affirmative message sequences with the environmental sounds only with the sleep programme being run separately.

In another embodiment of the present invention, the system 100 described above with reference to FIG. 1 may be modified for travelling so that the system 100 can be used to assist with overcoming jet lag. In that case, regardless of the destination of the user, by running a jet lag programme at 11 am local time and then running his/her selected sleep programme at his/her bedtime, the user can readily adjust to changes in time zones. The jet lag programme runs for a period of between 20 and 30 minutes and uses alpha and beta binaural beat frequencies.

Although the system of the present invention has been described with reference to specific elements in FIG. 1, it will readily be appreciated that the method for generating the sleep programmes as described above can be implemented on any electronic device having a memory and a processing unit. For example, the method may be implemented as an application (or program) for computers, laptops, notebooks, games consoles, smart phones and other electronic devices. In this case, the housing the display, the control panel and the speakers are provided by device onto which the application has been loaded and on which it is run to provide the sleep programmes as described above.

The system and method of the present invention may also be used to assist with the symptoms of sleep disorders, for example, depression, memory lapses, lack of concentration, anxiety, irritability, panic disorders and fatigue. In addition, some of the symptoms of the menopause may be alleviated by having the correct type of sleep as can be provided by the system in accordance with the present invention.

Sleep programmes in accordance with the present invention have been described, in a preferred embodiment, as being compiled from a plurality of components or parameters having different numbers of loops and loop run times. However, it will be appreciated that each programme may be stored as a continuous sound loop including each of the possible selections that a user may require, and selection of the desired sleep programme is played directly from memory without modification. In this case, each sleep programme may comprise a fixed sequence of binaural beat frequencies, each binaural beat frequency having a predefined duration within the fixed sequence.

Although the present invention has been described with predetermined numbers of loops being run for each programme, it will readily be understood that the number of loops and the frequencies used can be chosen in accordance with the particular device.

The invention claimed is:

1. A flexible sleep inducing and sleep maintenance system comprising:
   a housing;
   a control panel formed in the housing and configured for allowing input information to be provided for the selection of a sleep programme from a plurality of sleep programmes;
   a display formed in the housing and configured for displaying information relating to at least the selected sleep programme;
   a memory located within the housing and configured for storing a plurality of parameters relating to the plurality of sleep programmes, each of the parameters in the plurality of parameters comprising at least a binaural beat frequency and a number of repeated loops for each binaural beat frequency;
   a processing unit located within the housing and configured for:
      controlling the display and for processing input information received at the control panel relating to the selected sleep programme; and
      running the selected sleep programme thereon by selecting and retrieving the parameters from the memory based on the selected sleep programme, and, compiling the selected and retrieved parameters into the selected sleep programme in a specific order based on the selected sleep programme and in accordance with the input information received from the control panel such that the selected sleep programme comprises a specific sequence of the selected parameters compiled based on the selection of the selected sleep programme; and
   at least one pair of speaker units configured to relay the selected sleep programme to a user.

2. A system according to claim 1, wherein each repeated loop comprises a predetermined duration of time.

3. A system according to claim 1, wherein the plurality of sleep programmes comprises at least a deep sleep programme, and an alarm programme that comprises a deep sleep programme adjusted for an alarm time.

4. A system according to claim 3, wherein the deep sleep programme comprises binaural beat frequencies in alpha, delta and theta frequency bands.

5. A system according to claim 1, wherein each sleep programme further includes at least one of a subliminal message sequence and an affirmative message sequence running at the same time as the sequence of binaural beat frequencies for a portion of the sleep programme.

6. A system according to claim 5, wherein at least one of the subliminal message sequence and the affirmative message sequence is used when starting the selected sleep programme.

7. A system according to claim 5, wherein at least one of the subliminal message sequence and the affirmative message sequence is used at when ending the selected sleep programme.

8. A system according to claim 1, wherein each sleep programme further comprises a wake-up sequence comprising binaural beat frequencies in at least a beta frequency band.

9. A system according to claim 1, wherein the plurality of sleep programmes further comprises a power nap programme that comprises one of: a 30-minute programme; a 45-minute programme; and a 60-minute programme.

10. A system according to claim 9, wherein the power nap programme comprises binaural beat frequencies in at least alpha 01 and alpha 02 frequency bands with a wake-up sequence in a beta frequency band.

11. A system according to claim 10, wherein the 30-, 45- and 60-minute power nap programmes further comprise binaural beat frequencies in an alpha 03 frequency band.

12. A system according to claim 11, wherein each 30-, 45- and 60-minute power nap programmes further includes at least one of: a subliminal message sequence and an affirmative message sequence running at the same time as the sequence of binaural beat frequencies when starting the power nap programme.

13. A system according to claim 1, wherein the plurality of sleep programmes further comprises a falling asleep programme.

14. A system according to claim 13, wherein the falling asleep programme comprises binaural beat frequencies in alpha, delta and theta frequency bands.

15. A system according to claim 1, wherein the plurality of sleep programmes further comprises a jet lag sleep programme of binaural beat frequencies in alpha and beta frequency bands.

16. A system according to claim 1, wherein a selected environmental sound is played for the duration of the selected sleep programme.

17. A system according to claim 16, wherein the selected environmental sound comprises one of: a background sound and a non-discernible sound.

18. A system according to claim 1, wherein the at least one pair of speaker units is formed in the housing.

19. A system according to claim 1, wherein the at least one pair of speaker units is separated from the housing and is connected thereto to receive signals corresponding to the selected sleep programme.

20. A system according to claim 1, wherein the parameters stored in the memory further comprise a plurality of environmental sounds and loops of the environmental sounds.

21. A system according to claim 1, wherein the parameters stored in the memory further comprise at least one of: a subliminal message sequence and an affirmative message sequence.

22. A system according to claim 1, wherein the plurality of sleep programmes comprises a 15-minute power nap programme.

23. A system according to claim 22, wherein the 15-minute power nap programme comprises binaural beat frequencies in at least alpha 01 and alpha 02 frequency bands with a wake-up sequence in a beta frequency band.

24. A method for inducing and maintaining sleep in an individual in accordance with a selected sleep programme, the method comprising the steps of:
  receiving, at a processing unit, input information relating to the selected sleep programme: and
  running, by the processing unit, the selected sleep programme to expose the individual to the selected sleep programme by:
    a) determining a specific sequence of binaural beat frequencies based on a selection of the selected sleep programme selected from a plurality of sleep programmes;
    b) determining a number of loops for each binaural beat frequency in the specific sequence of binaural beat frequencies based on the selection of the selected sleep programme; and
    c) compiling the specific sequence of binaural beat frequencies based on the selection of the selected sleep programme, each binaural beat frequency being run for the determined number of loops to provide a compiled selected sleep programme, the compiled sleep programme comprising the specific sequence of binaural beat frequencies played for the determined number of repeated loops in accordance with the selection of the selected sleep programme.

25. A method according to claim 24, wherein the input information comprises a selection of an environmental sound, and the compiling step comprises compiling the specific sequence of binaural beat frequencies with the selected environmental sound for the entire duration of the selected sleep programme.

26. A method according to claim 24, further comprising the step of compiling the sequence of binaural beat frequencies with a selected environmental sound, the environmental sound running simultaneously with the sequence of binaural beat frequencies.

27. A method of compiling a selected sleep programme for an individual, the method comprising the steps of:
  receiving, at a processor unit, input information relating to a selected sleep programme selected from a plurality of sleep programmes; and
  running, at the processor unit, the selected sleep programme in accordance with the input information by performing the following steps:
    a) selecting a specific sequence of binaural beat frequencies based on the selection of the selected sleep programme;
    b) determining a number of loops for each binaural beat frequency in the specific sequence of binaural beat frequencies based on the selection of the selected sleep programme; and
    c) compiling the specific sequence of binaural beat frequencies with the determined number of loops for each binaural beat frequency based on the selection of the selected sleep programme.

28. A method according to claim 27, further comprising the step of adjusting the sequence of binaural beat frequencies in accordance with a predefined wake-up time.

29. A method according to claim 27, further comprising the step of adjusting the number of loops for each binaural beat frequency in the sequence of binaural beat frequencies in accordance with a predefined wake-up time.

30. A method according to claim 27, further comprising the step of adding at least one subliminal message sequence during the compiling step in accordance with the selected sleep programme.

31. A method according to claim 27, further comprising the step of adding at least one affirmative message sequence during the compiling step in accordance with the selected sleep programme.

32. A method according to claim 27, further comprising the step of adding an environmental sound during the compiling step in accordance with the selected sleep programme.

33. A computer program product comprising a non-transitory tangible storage medium configured for storing instructions for causing a computer system to execute a method for inducing and maintaining sleep in an individual in accordance with a selected sleep programme, the method comprising the steps of receiving, at the computer system, input information relating to the selected sleep programme, and running, by the computer system, the selected sleep programme to expose the individual to the selected sleep programme by:
  a) determining a specific sequence of binaural beat frequencies based on selection of the selected sleep programme from a plurality of sleep programmes:
  b) determining a number of loops for each binaural beat frequency in the specific sequence of binaural beat frequencies based on the selection of the selected sleep programme; and
  c) compiling the specific sequence of binaural beat frequencies based on the selection of the selected sleep programme, each binaural beat frequency being run for the determined number of loops to provide a compiled selected sleep programme, the compiled selected sleep programme comprising the specific sequence of binaural beat frequencies run for the determined number of repeated loops in accordance with the selection of the selected sleep programme.

* * * * *